US010174319B2

(12) United States Patent
Matsuo et al.

(10) Patent No.: US 10,174,319 B2
(45) Date of Patent: Jan. 8, 2019

(54) NUCLEIC ACID DRUG FOR INDUCING SKIPPING OF VARIANT EXON OF CD44 GENE AND INCREASING EXPRESSION OF NORMAL TYPE CD44 MRNA

(71) Applicants: KNC LABORATORIES CO., LTD., Kobe-shi, Hyogo (JP); KOBE GAKUIN EDUCATIONAL FOUNDATION, Kobe-shi, Hyogo (JP)

(72) Inventors: Masafumi Matsuo, Kobe (JP); Seiji Matsuda, Kobe (JP)

(73) Assignees: KNC LABORATORIES CO., LTD., Kobe-shi (JP); KOBE GAKUIN EDUCATIONAL FOUNDATION, Kobe-shi (JP)

( * ) Notice: Subject to any disclaimer, the term of this patent is extended or adjusted under 35 U.S.C. 154(b) by 0 days.

(21) Appl. No.: 15/309,588

(22) PCT Filed: May 13, 2015

(86) PCT No.: PCT/JP2015/063810
§ 371 (c)(1),
(2) Date: Nov. 8, 2016

(87) PCT Pub. No.: WO2015/178277
PCT Pub. Date: Nov. 26, 2015

(65) Prior Publication Data
US 2017/0137810 A1    May 18, 2017

(30) Foreign Application Priority Data
May 19, 2014    (JP) .................................. 2014-103674

(51) Int. Cl.
| | |
|---|---|
| A61K 48/00 | (2006.01) |
| C07H 21/02 | (2006.01) |
| C07H 21/04 | (2006.01) |
| C12N 15/113 | (2010.01) |
| A61K 31/7088 | (2006.01) |
| A61K 31/7115 | (2006.01) |
| A61K 31/712 | (2006.01) |

(52) U.S. Cl.
CPC ........ *C12N 15/113* (2013.01); *A61K 31/7088* (2013.01); *A61K 31/712* (2013.01); *A61K 31/7115* (2013.01); *A61K 48/00* (2013.01); *C12N 2310/111* (2013.01); *C12N 2310/314* (2013.01); *C12N 2310/321* (2013.01); *C12N 2310/3231* (2013.01); *C12N 2320/33* (2013.01)

(58) Field of Classification Search
CPC .................... A61K 31/713; C12N 2310/11
See application file for complete search history.

(56) References Cited

U.S. PATENT DOCUMENTS

| 2003/0170637 A1 | 9/2003 | Pirrung et al. |
| 2010/0120022 A1* | 5/2010 | Ayalon-Soffer et al. ..................... C12N 15/111 |
| 2013/0211062 A1 | 8/2013 | Watanabe et al. |
| 2014/0343266 A1 | 11/2014 | Watanabe et al. |

FOREIGN PATENT DOCUMENTS

| JP | 2014-054250 A | 3/2014 | |
| WO | WO 2006/059507 A1 | 6/2006 | |
| WO | WO 2006/076021 A2 | 7/2006 | |
| WO | WO 2008/029619 A1 * | 3/2008 | ........... C12N 15/113 |
| WO | WO 2008/029619 A1 | 3/2008 | |
| WO | WO 2013/100190 A1 * | 4/2013 | ........... C12N 15/113 |
| WO | WO 2013/100190 A1 | 7/2013 | |

OTHER PUBLICATIONS

International Preliminary Report on Patentability and the English translation of the Written Opinion of the International Searching Authority, (Forms PCT/IB/338, PCT/IB/373 and PCT/ISA/237), dated Dec. 1, 2016, for International Application No. PCT/JP2015/063810.

International Search Report (PCT/ISA/210) issued in PCT/JP2015/063810, dated Jul. 21, 2015.

Ishimoto et al, "CD44 Variant Regulates Redox Status in Cancer Cells by Stabilizing the xCT Subunit of System xc and Thereby Promotes Tumor Growth", Cancer Cell, vol. 19, No. 3, Mar. 15, 2011, pp. 387-340.

(Continued)

*Primary Examiner* — Amy H Bowman
(74) *Attorney, Agent, or Firm* — Birch, Stewart, Kolasch & Birch, LLP

(57) ABSTRACT

Insertion of variant exons of CD44 gene of cancer stem cells into its mRNA is inhibited whereupon the cancer stem cells lose their properties so that they are rendered sensitive to anticancer agents and radiation, possibly leading to cancer treatment.

A drug for cancer treatment, comprising an antisense oligonucleotide capable of inducing skipping of variant exon(s) of CD44 gene to thereby increase expression of normal CD44 mRNA, a pharmaceutically acceptable salt thereof, a solvate thereof or a prodrug thereof. An oligonucleotide of 20-23 bp having the entirety or a part of any one of the nucleotide sequences as shown in SEQ ID NOS: 1 to 19, a pharmaceutically acceptable salt thereof, a solvate thereof or a prodrug thereof. A drug for inducing skipping of at least one variant exon selected from the group consisting of variant exons 8, 9 and 10 of CD44 gene, comprising the above-described oligonucleotide, a pharmaceutically acceptable salt thereof, a solvate thereof or a prodrug thereof.

13 Claims, 7 Drawing Sheets

Specification includes a Sequence Listing.

(56) References Cited

OTHER PUBLICATIONS

Matsuda et al., "Kato III Saibo no CD44 no Seijoka o Mezashita ENA Oligo Kakusan ni yoru Variant Exon no Skipping Yudo", Abstracts of Annual Meeting of Pharmaceutical Society of Japan, Mar. 2015, 135th, p. ROMBUNNO.28PB-am115.
Wrriten Opinion (PCT/ISA/237) issued in PCT/JP2015/063810, dated Jul. 21, 2015.
Extended European Search Report for European Application No. 15796807.4, dated Nov. 13, 2017.
Harada et al., "Introduction of Antisense CD44S CDNA Down-Regulates Expression of Overall CD44 Isoforms and Inhibits Tumor Growth and Metastasis in Highly Metastatic Colon Carcinoma Cells," Int. J. Cancer, vol. 91, XP-002223971, 2001, pp. 67-75.
Naor et al., "CD44 in Cancer," Critical Reviews in Clinical Laboratory Sciences, vol. 39, No. 6, XP008074744, Jan. 2002, pp. 527-579.
Rall et al., "CD44 Isoform Expression in Primary and Metastatic Pancreatic Adenocarcinoma," Cancer Research, vol. 55, XP55419327, May 1, 1995, pp. 1831-1835.
Reeder et al., "Expression of Antisense CD44 Variant 6 Inhibits Colorectal Tumor Metastasis and Tumor Growth in a Wound Environment," Cancer Research, vol. 58, XP008154207, Aug. 15, 1998, pp. 3719-3726.

\* cited by examiner

NUCLEIC ACID DRUG FOR INDUCING SKIPPING OF VARIANT EXON OF CD44 GENE AND INCREASING EXPRESSION OF NORMAL TYPE CD44 MRNA

TECHNICAL FIELD

The present invention relates to a nucleic acid drug which induces skipping of variant exons of CD44 gene to thereby increase expression of normal CD44 mRNA.

BACKGROUND ART

Recently, cancer stem cells have been attracting attention in the field of cancer therapy and research. These cancer stem cells are said to be a cause that induces resistance against therapy or recurrence/metastasis of cancer.

An adhesion molecule CD44 of which ligand is hyaluronic acid and which is expressed in the cell membrane in cancer stem cells is a cancer stem cell marker and involved in their properties as cancer stem cells.

CD44 gene comprises 20 exons and produces various variant isoforms through alternative splicing (FIG. 1). It is believed that CD44 variant isoforms (especially, CD44v8-10 comprising variant exons 8, 9 and 10) that are produced from CD44 variant mRNAs bind to cystine transporter xCT in the cell membrane, promote cystine uptake and increase the level of intracellular glutathione (antioxidant), thereby enhancing the resistance against oxidation stress of anticancer agents and radiation (FIG. 2). Insertion of these variant exons is not caused by abnormalities in the genomic sequence but caused by abnormalities in a certain splice regulator specific to cancer stem cells (Non-Patent Document No. 1).

PRIOR ART LITERATURE

Non-Patent Document

Non-Patent Document No. 1: Cancer Cell 19, 387-400, Mar. 15, 2011

DISCLOSURE OF THE INVENTION

Problem for Solution by the Invention

It is an object of the present invention to treat cancer by inhibiting insertion of variant exons into the mRNA of CD44 gene in cancer stem cells to thereby eliminate the properties of the cancer stem cells and make these cells sensitive to anticancer agents and radiation.

Means to Solve the Problem

As a result of intensive and extensive research efforts, the present inventors, who started with cancer stem cells that had become stem cells upon producing abnormal CD44 isoforms on account of insertion of variant exons into CD44 gene due to genetic abnormalities, could successfully directed the production of CD44v mRNA encoding abnormal CD44 isoforms to the production of normal CD44 mRNA by skipping of variant exons. Thus, the present invention has been achieved. Briefly, antisense oligonucleotides (AOs) complementary to exon sequences bind to the sequences to thereby inhibit the binding of nucleic proteins to mRNA precursors. Through these procedures, AOs inhibit the mode of splicing regulation and induce skipping of any desired exon(s). The variant mRNAs of CD44 gene are generated by abnormalities in splice regulators specific to cancer stem cells. The present invention induces exon skipping by inhibiting the mode of such splicing regulation with AOs and promotes production of normal CD44.

A summary of the present invention is as described below.

(1) A drug for cancer treatment, comprising an antisense oligonucleotide capable of inducing skipping of variant exon(s) of CD44 gene to thereby increase expression of normal CD44 mRNA, a pharmaceutically acceptable salt thereof, a solvate thereof or a prodrug thereof (2) The drug for cancer treatment according to (1) above, which enhances the sensitivity of cancer cells to anticancer agents and/or radiation.

(3) The drug for cancer treatment according to (1) or (2) above, wherein the target variant exon to be skipped is at least one selected from the group consisting of variant exons 8, 9 and 10.

(4) The drug for cancer treatment according to (3) above, wherein the antisense oligonucleotide is an oligonucleotide having a nucleotide sequence complementary to a part or the entirety of the nucleotide sequence of variant exon 8, 9 or 10 of CD44 gene.

(5) The drug for cancer treatment according to (4) above, wherein the oligonucleotide having a nucleotide sequence complementary to a part or the entirety of the nucleotide sequence of variant exon 8, 9 or 10 of CD44 gene is an oligonucleotide of 20-23 bp having the entirety or a part of any one of the nucleotide sequences as shown in SEQ ID NOS: 1 to 19.

(6) The drug for cancer treatment according to any one of (1) to (5) above, wherein the antisense oligonucleotide comprises at least one modified nucleotide.

(7) The drug for cancer treatment according to (6) above, wherein D-ribofuranose constituting the modified nucleotide is 2'-O, 4'-C-alkylenated.

(8) An oligonucleotide of 20-23 bp having the entirety or a part of any one of the nucleotide sequences as shown in SEQ ID NOS: 1 to 19, a pharmaceutically acceptable salt thereof, a solvate thereof or a prodrug thereof (9) The oligonucleotide according to (8) above comprising at least one modified nucleotide, a pharmaceutically acceptable salt thereof, a solvate thereof or a prodrug thereof

(10) The oligonucleotide according to (9) above, wherein D-ribofuranose constituting the modified nucleotide is 2'-O, 4'-C-alkylenated, a pharmaceutically acceptable salt thereof, a solvate thereof or a prodrug thereof

(11) The oligonucleotide according to any one of (8) to (10) above which is an antisense oligonucleotide targeting variant exon(s) of CD44 gene, a pharmaceutically acceptable salt thereof, a solvate thereof or a prodrug thereof

(12) A drug for inducing skipping of at least one variant exon selected from the group consisting of variant exons 8, 9 and 10 of CD44 gene, comprising the oligonucleotide according to any one of (8) to (11) above, a pharmaceutically acceptable salt thereof, a solvate thereof or a prodrug thereof

(13) A method of treating cancer, comprising administering to a subject a pharmaceutically effective amount of an antisense oligonucleotide capable of inducing skipping of variant exon(s) of CD44 gene to thereby increase expression of normal CD44 mRNA, a pharmaceutically acceptable salt thereof, a solvate thereof or a prodrug thereof

(14) Use of an antisense oligonucleotide capable of inducing skipping of variant exon(s) of CD44 gene to thereby increase expression of normal CD44 mRNA, a pharmaceutically acceptable salt thereof, a solvate thereof or a prodrug thereof, for treating cancer.

(15) An antisense oligonucleotide capable of inducing skipping of variant exon(s) of CD44 gene to thereby increase expression of normal CD44 mRNA, a pharmaceutically acceptable salt thereof, a solvate thereof or a prodrug thereof, for use in a method of treating cancer.

Effect of the Invention

Addition of AO to cancer stem cells induces exon skipping, whereupon the level of CD44v mRNA is decreased and production of normal CD44 mRNA is increased in cancer stem cells which have been producing CD44v mRNA. Upon production of normal CD44 protein, sensitivity to anticancer agents and radiation therapy is recovered and complete cure of cancer is expected.

The present specification encompasses the contents disclosed in the specification and/or the drawings of Japanese Patent Application No. 2014-103674 based on which the present patent application claims priority.

A CD44 variant isoform (CD44v8-10) produced from CD44 variant (CD44v8-10) mRNA binds to cystine transporter xCT in the cell membrane, promotes uptake of cystine and increases the level of intracellular glutathione (antioxidant), thereby enhancing the resistance to the oxidation stress of anticancer agents and radiation.

Figure 1:
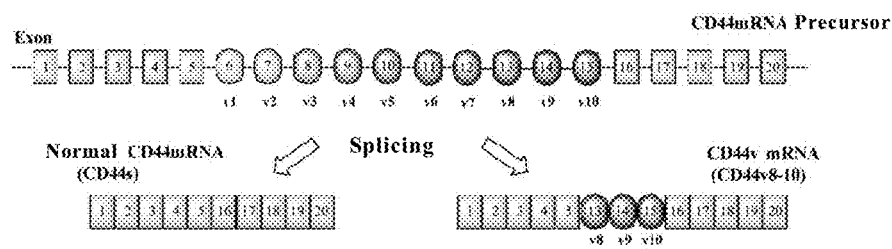
FIG. 1 A schematic drawing showing that CD44 gene comprises 20 exons and produces CD44 variant mRNA (CD44v8-10) through alternative splicing FIG. 2 A schematic drawing showing the mechanism underlying the CD44 variant tolerance of cancer stem cells.
Figure 2:
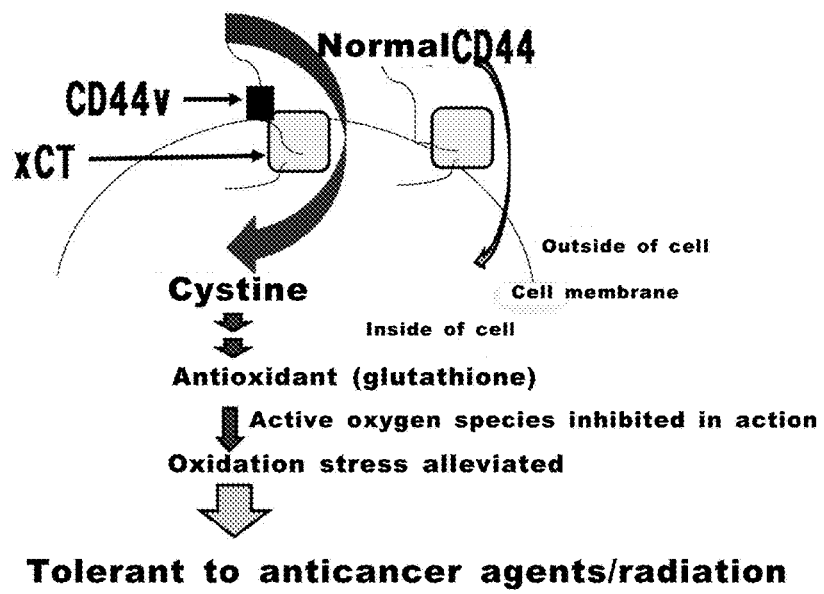
Figure 3:
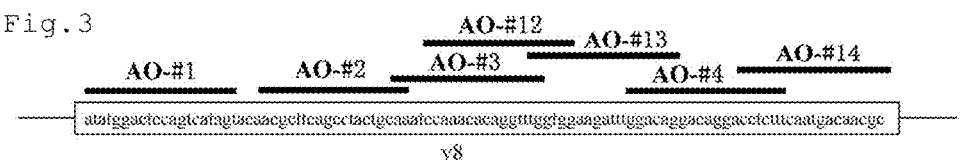

FIG. 3 This Figure shows the locations of the sequences of AOs (AO-#1 to -#4 and AO-#12 to -#14) synthesized in Examples described later which are complementary to CD44v8 mRNA. The nucleotide sequences of AO-#1 to -#4 are shown in SEQ ID NOS: 1 to 4, respectively. The nucleotide sequence of CD44v8 mRNA is shown in SEQ ID NO: 20.

Figure 4:
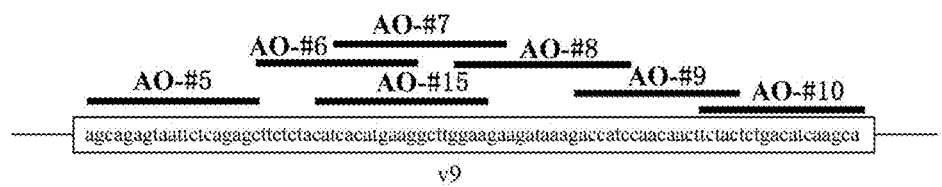

FIG. 4 This Figure shows the locations of the sequences of AOs (AO-#5 to -#10 and AO-#15) synthesized in Examples described later which are complementary to CD44v9 mRNA. The nucleotide sequences of AO-#5 to -#10 are shown in SEQ ID NOS: 5 to 10, respectively. The nucleotide sequence of CD44v9 mRNA is shown in SEQ ID NO: 21.

Figure 5:
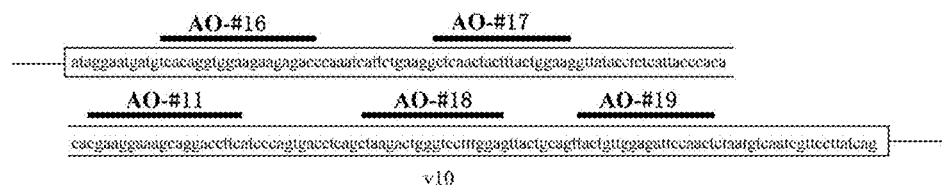

FIG. 5 This Figure shows the locations of the sequences of AOs (AO-#11 and AO-#16 to -#19) synthesized in Examples described later which are complementary to CD44v10 mRNA. The nucleotide sequence of AO-#11 is shown in SEQ ID NO: 11. The nucleotide sequence of CD44v10 mRNA is shown in SEQ ID NO: 22.

Figure 6:
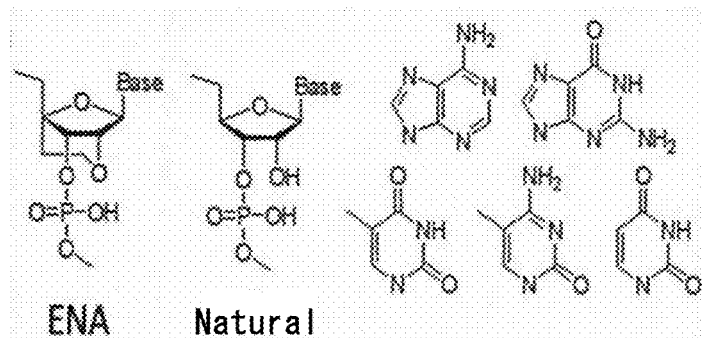

FIG. 6 This Figure shows the structure of ENA™ (2'-O, 4'-C-Ethylene-bridged Nucleic Acids).

Figure 7:
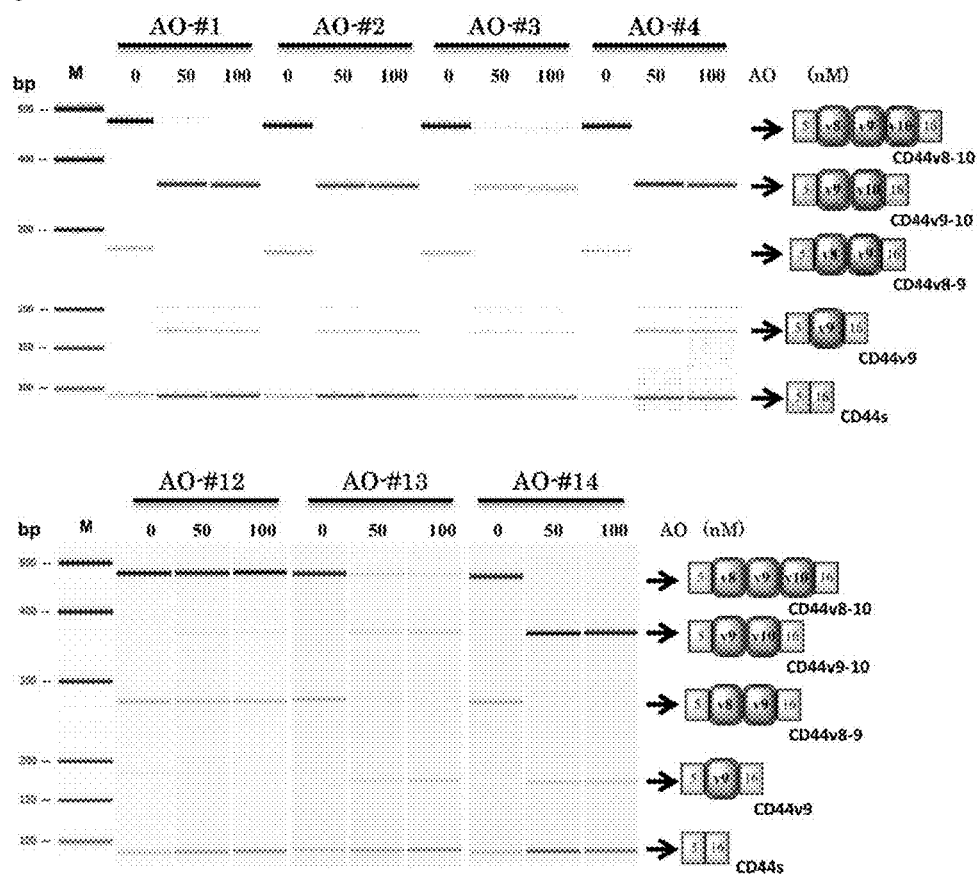

FIG. 7 This Figure shows the effect of exon skipping induction with AOs (AO-#1 to -#4 and AO-#12 to -#14) which are complementary to CD44v8 mRNA sequence in KATOIII cells.

Figure 8:
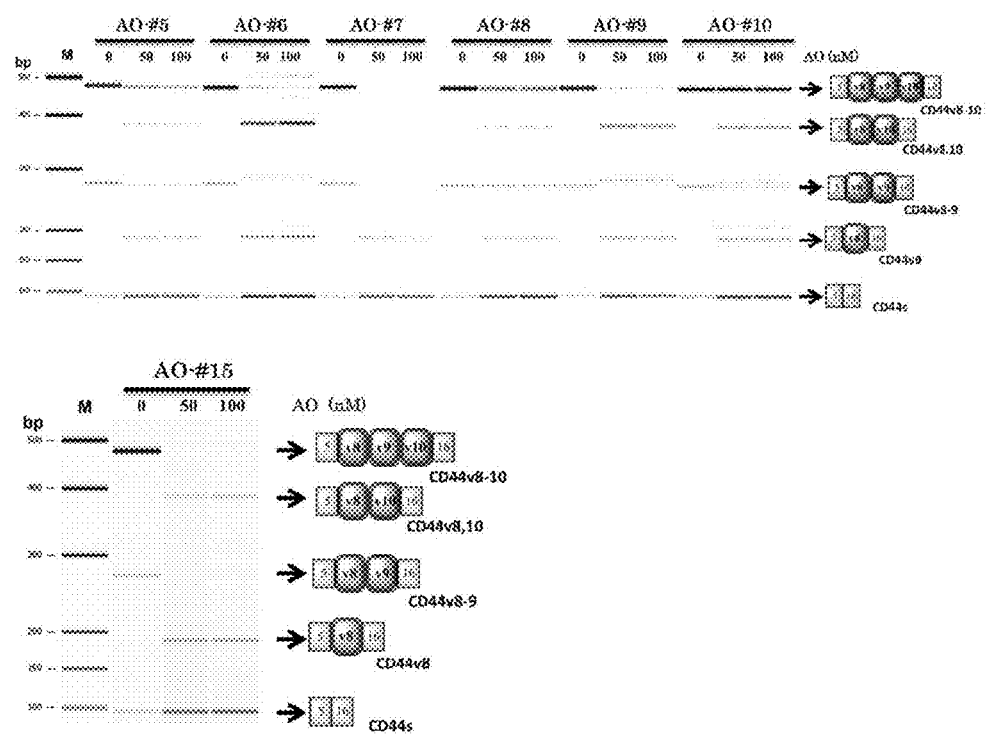

FIG. 8 This Figure shows the effect of exon skipping induction with AOs (AO-#5 to -#10 and AO-#15) which are complementary to CD44v9 mRNA sequence in KATOIII cells.

Figure 9:
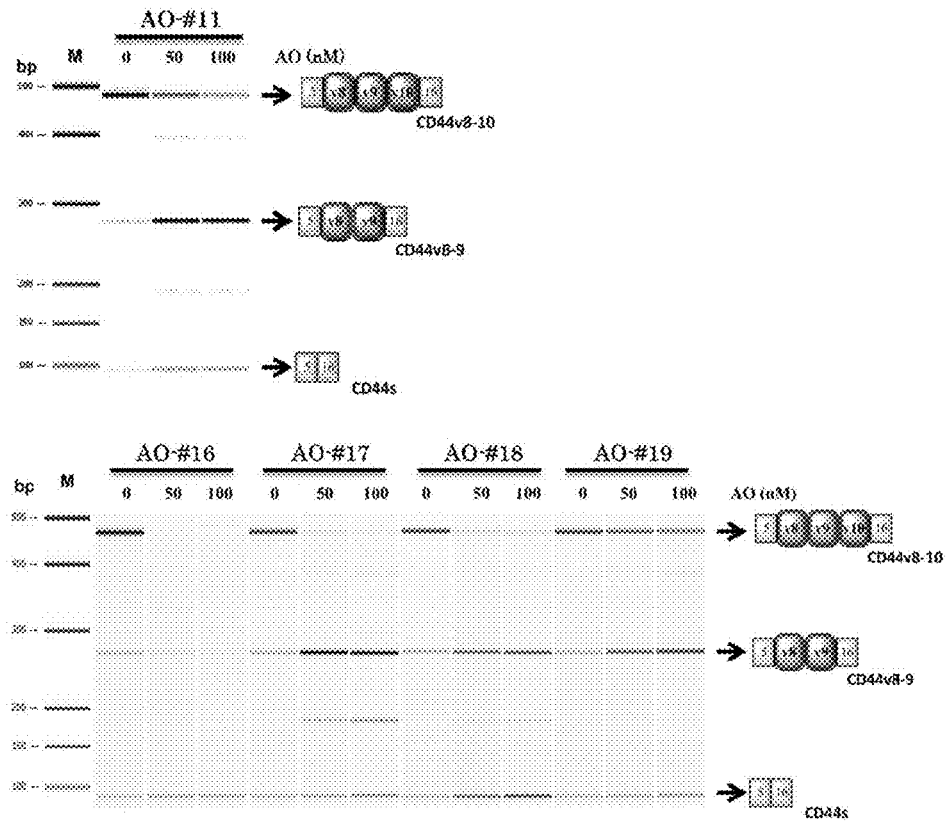

FIG. 9 This Figure shows the effect of exon skipping induction with AOs (AO-#11 and AO-#16 to -#19) which are complementary to CD44v10 mRNA sequence in KATOIII cells.

Figure 10:
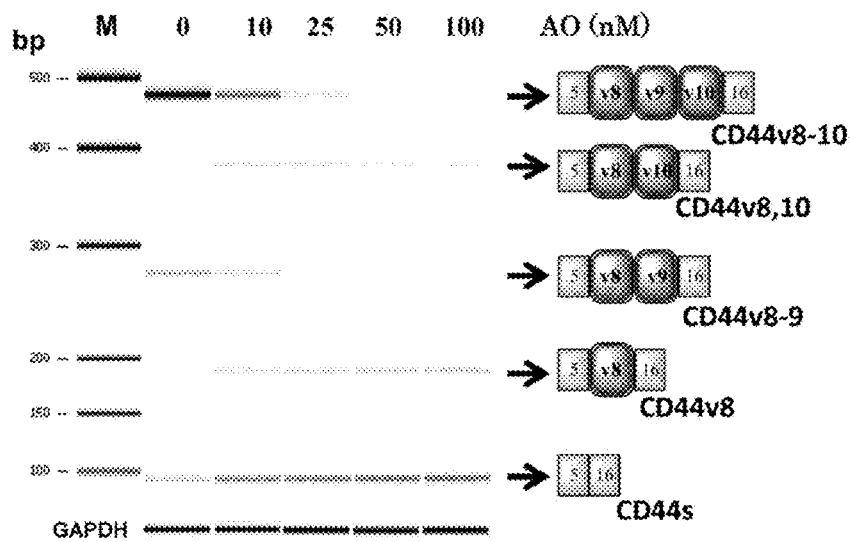

FIG. 10 This Figure shows the results of AO-#7 (10 nM, 25 nM, 50 nM and 100 nM) which exhibited the highest exon skipping induction effect.

Figure 11:
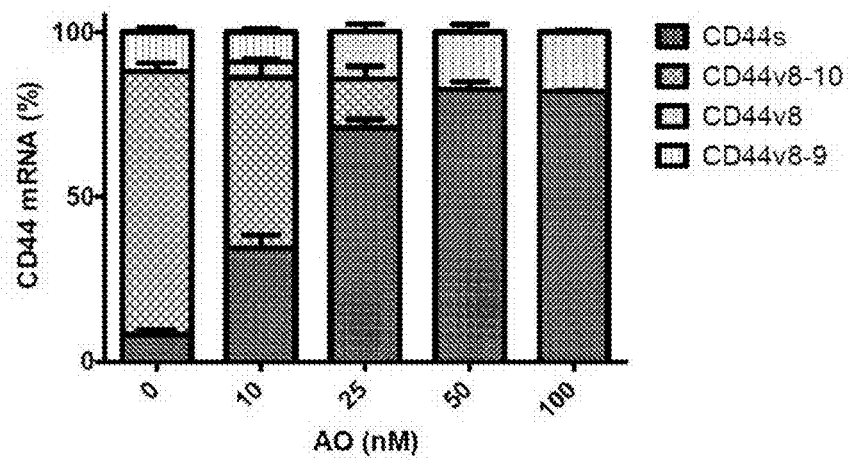

FIG. 11 This Figure shows graphically the results of AO-#7 (10 nM, 25 nM, 50 nM and 100 nM) that exhibited the highest exon skipping induction effect.

Figure 12:
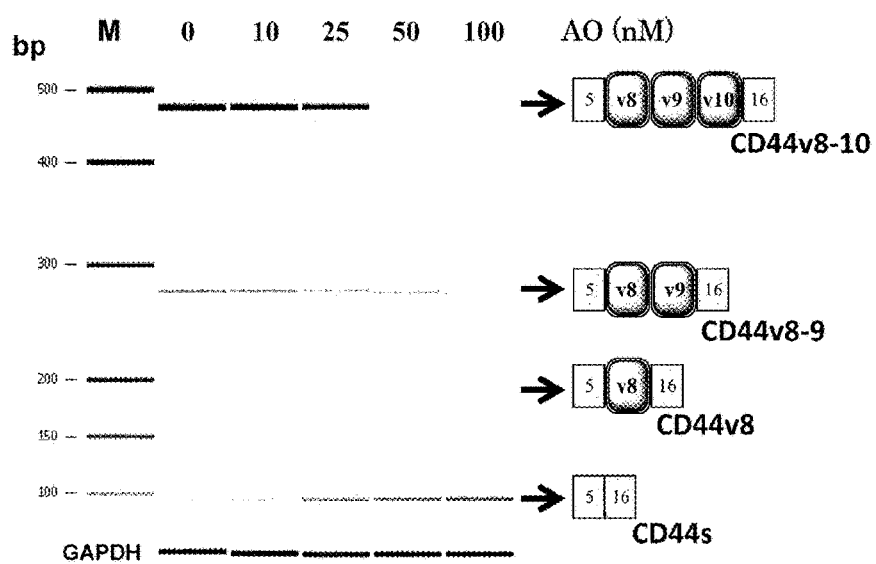

FIG. 12 This Figure shows the effect of exon skipping induction with AO (AO-#7) which is complementary to CD44v9 mRNA sequence in HT29 cells.

Figure 13:
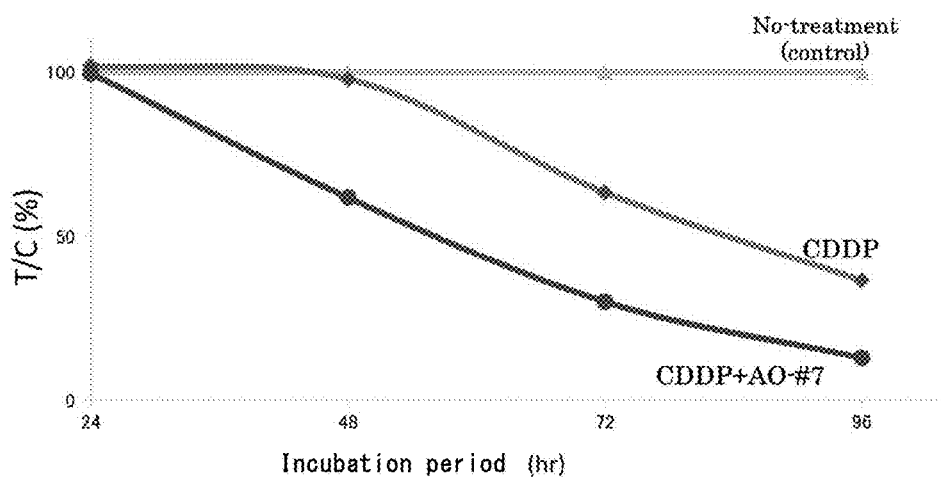

FIG. 13 This Figure shows the growth inhibition effect on cancer cell (KATOIII cells) by improving the resistance to CDDP (cisplatin) treatment using AO-#7 which was the most effective in inducing the exon skipping of CV44v mRNA.

Figure 14:
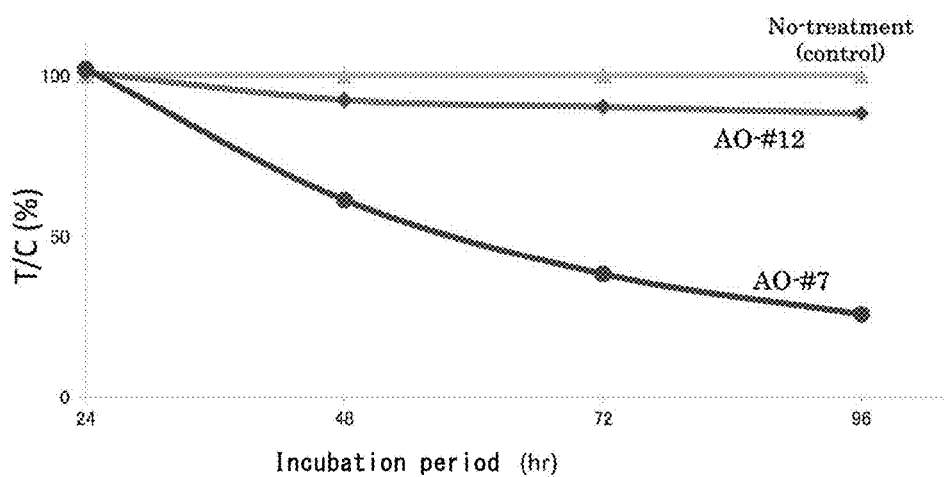

FIG. 14 This Figure shows a comparison of cancer cell (KATOIII cells) growth inhibition effects of AO-#7 which was the most effective in inducing the exon skipping of CD44v mRNA and AO-#12 which scarcely affected the exon skipping of CD44v9 mRNA.

BEST MODES FOR CARRYING OUT THE INVENTION

Hereinbelow, embodiments of the present invention will be described in more detail.

The present invention provides a drug for cancer treatment comprising an antisense oligonucleotide capable of inducing skipping of variant exon(s) of CD44 gene to thereby increase expression of normal CD44 mRNA, a pharmaceutically acceptable salt thereof, a solvate thereof or a prodrug thereof.

The drug for cancer treatment of the present invention may target cancers that express variant exons of CD44 gene. Specific examples of such cancers include, but are not limited to, gastric cancer, colon cancer, breast cancer, lung cancer, bladder cancer, thyroid cancer, and head and neck squamous cell carcinoma. Among these, cancers expressing at least one of the variant exons CD44v8, CD44v9 and CD44v10 are preferable. Specific examples of such cancers include, but are not limited to, gastric cancer, colon cancer, breast cancer, lung cancer, and head and neck squamous cell carcinoma.

Since the drug for cancer treatment of the present invention is capable of enhancing the sensitivity of cancer cells to anticancer agents and/or radiation, the drug of the present invention may be administered to patients jointly with chemotherapy or radiation therapy.

The target variant exon to be skipped with the drug for cancer treatment of the present invention may be at least one selected from the group consisting of variant exons 8, 9 and 10.

In the drug for cancer treatment of the present invention, the antisense oligonucleotide may target variant exon(s) of CD44 gene. For example, the antisense oligonucleotide may be an oligonucleotide comprising a nucleotide sequence complementary to a sequence consisting of 20-23 consecutive nucleotides in the nucleotide sequence encoding variant 8, 9 or 10 of CD44 gene. Briefly, the antisense oligonucleotide may be an oligonucleotide having a nucleotide sequence complementary to a part or the entirety of the nucleotide sequence of variant exon 8, 9 or 10 of CD44 gene. The nucleotide sequences of the mRNAs of variant exons of 8, 9 and 10 of CD44 gene are shown in SEQ ID NOS: 20 to 22, respectively.

The oligonucleotide having a nucleotide sequence complementary to a part or the entirety of the nucleotide sequence of variant exon 8, 9 or 10 of CD44 gene may be exemplified by those which have the entirety or a part of the nucleotide sequence of any one of SEQ ID NOS: 1 to 19. The length of such oligonucleotides is suitably 18-25 bp, preferably 18-23 bp, and more preferably 20-23 bp.

Nucleotides constituting the antisense oligonucleotide may be either natural DNA, natural RNA, or modified DNA or RNA. Preferably, at least one of the nucleotides is a modified nucleotide.

Examples of modified nucleotide include those nucleotides in which sugar is modified (e.g., D-ribofuranose is 2'-O-alkylated or D-ribofuranose is 2'-O, 4'-C-alkylenated), those nucleotides in which phosphodiester bond is modified (e.g., thioated), those nucleotides in which base is modified, a combination of above-described nucleotides, and so forth. Antisense oligonucleotides in which at least one D-ribofuranose constituting the oligonucleotides is 2'-O-alkylated or 2'-O,4'-C-alkylenated have high binding strength to RNA and high resistance to nuclease. Thus, they are expected to produce higher therapeutic effect than natural nucleotides (i.e. oligo DNA or oligo RNA). Further, oligonucleotides in which at least one phosphodiester bond constituting the oligonucleotides is thioated also have high resistance to nuclease and, thus, are expected to produce higher therapeutic effect than natural nucleotides (i.e. oligo DNA or oligo RNA). Oligonucleotides comprising both the modified sugar and the modified phosphate as described above have still higher resistance to nuclease and, thus, are expected to produce still higher therapeutic effect.

With respect to the antisense oligonucleotide, examples of modified sugars include, but are not limited to, D-ribofuranose as 2'-O-alkylated (e.g. 2'-O-methylated, 2'-O-aminoethylated, 2'-O-propylated, 2'-O-allylated, 2'-O-methoxyethylated, 2'-O-butylated, 2'-O-pentylated, or 2'-O-propargylated); D-ribofuranose as 2'-O,4'-C-alkylenated (e.g. 2'-O,4'-C-ethylenated, 2'-O,4'-C-methylenated, 2'-O,4'-C-propylenated, 2'-O,4'-C-tetramethylated, or 2'-O,4'-C-pentamethylated); 3'-deoxy-3'-amino-2'-deoxy-D-ribofuranose; and 3'-deoxy-3'-amino-2'-deoxy-2'-fluoro-D-ribofuranose.

With respect to the antisense oligonucleotide, examples of the modification of phosphodiester bond include, but are not limited to, phosphorothioate bond, methylphosphonate bond, methylthiophosphonate bond, phosphorodithioate bond and phosphoroamidate bond.

Examples of modified bases include, but are not limited to, cytosine as 5-methylated, 5-fluorinated, 5-brominated, 5-iodinated or N4-methylated; thymidine as 5-demethylated (uracil), 5-fluorinated, 5-brominated or 5-iodinated; adenine as N6-methylated or 8-brominated; and guanine as N2-methylated or 8-brominated.

The term "pharmaceutically acceptable salt" as used herein refers to salts of the antisense oligonucleotide. Examples of such salts include, but are not limited to, alkaline metal salts such as sodium salts, potassium salts or lithium salts; alkaline earth metal salts such as calcium salts or magnesium salts; metal salts such as aluminum salts, iron salts, zinc salts, copper salts, nickel salts or cobalt salts; amine salts including inorganic salts such as ammonium salts and organic salts such as t-octylamine salts, dibenzylamine salts, morpholine salts, glucosamine salts, phenylglycine alkyl ester salts, ethylenediamine salts, N-methylglucamine salts, guanidine salts, diethylamine salts, triethylamine salts, dicyclohexylamine salts, N,N'-dibenzylethylenediamine salts, chloroprocaine salts, procaine salts, diethanolamine salts, N-benzyl-phenethylamine salts, piperazine salts, tetramethylammonium salts or tris(hydroxymethyl)aminomethane salts; inorganic acid salts including hydrohalogenic acid salts such as hydrofluorides, hydrochlorides, hydrobromides or hydroiodides, nitrates, perchlorates, sulfates or phosphates; organic acid salts including lower alkane sulfonic acid salts such as methanesulfonates, trifluoromethanesulfonates or ethanesulfonates, arylsulfonic acid salts such as benzenesulfonates or p-toluenesulfonates, acetates, malates, fumarates, succinates, citrates, tartrates, oxalates or maleates; and amino acid salts such as glycine salts, lysine salts, arginine salts, ornithine salts, glutamic acid salts or aspartic acid salts. These salts may be prepared by known methods.

The antisense oligonucleotide sometimes occurs as a solvate (e.g., hydrate). The antisense oligonucleotide of the present invention may be such a solvate.

Further, the antisense oligonucleotide may be administered in the form of a prodrug. Examples of such prodrug include, but are not limited to, amides, esters, carbamates, carbonates, ureides and phosphates. These prodrugs may be prepared by known methods.

The antisense oligonucleotide may be synthesized with a commercially available DNA synthesizer (e.g., PerkinElmer Model 392 based on the phosphoramidite method) according to the method described in Nucleic Acids Research, 12, 4539 (1984) with necessary modifications. As phosphoramidite reagents to be used in the process, natural nucleosides and 2'-O-methylnucleosides (i.e., 2'-O-methylguanosine, 2'-O-methyladenosine, 2'-O-methylcytosine and 2'-O-methyluridine) are commercially available. As regards 2'-O-alkylguanosine, -alkyladenosine, -alkylcytosine and -alkyluridine in which the carbon number of the alkyl group is 2-6, the following methods may be employed.

2'-O-aminoethylguanosine, -aminoethyladenosine, -aminoethylcytosine and -aminoethyluridine may be synthesized as previously described (Blommers et al., Biochemistry (1998), 37, 17714-17725).

2'-O-propylguanosine, -propyladenosine, -propylcytosine and -propyluridine may be synthesized as previously described (Lesnik, E. A. et al., Biochemistry (1993), 32, 7832-7838).

For the synthesis of 2'-O-allylguanosine, -allyladenosine, -allylcytosine and -allyluridine, commercially available reagents may be used.

2'-O-methoxy ethylguanosine, -methoxyethyladenosine, -methoxyethylcytosine and -methoxyethyluridine may be synthesized as previously described (U.S. Pat. No. 6,261,840 or Martin, P. Helv. Chim. Acta. (1995) 78, 486-504).

2'-O-butylguanosine, -butyladenosine, -butylcytosine and -butyluridine may be synthesized as previously described (Lesnik, E. A. et al., Biochemistry (1993), 32, 7832-7838).

2'-O-pentylguanosine, -pentyladenosine, -pentylcytosine and -pentyluridine may be synthesized as previously described (Lesnik, E. A. et al., Biochemistry (1993), 32, 7832-7838).

For the synthesis of 2'-O-propargylguanosine, -propargyladenosine, propargylcytosine and -propargyluridine, commercially available reagents may be used.

2'-O,4'-C-methyleneguanosine, 2'-O,4'-C-methyleneadenosine, 5-methylcytosine and 5-methylthymidine may be prepared according to the method described in WO99/14226; and 2'-O,4'-C-alkyleneguanosine, 2'-O,4'-C-alkyleneadenosine, 5-methylcytosine and 5-methylthymidine in which the carbon number of the alkylene group is 2-5 may be prepared according to the method described in WO00/47599.

An antisense oligonucleotide with phosphorothioate bonds can be synthesized by coupling phosphoramidite reagents and then reacting sulfur, tetraethylthiuram disulfide (TDTD; Applied Biosystems), Beaucage reagent (Glen Research) or a reagent such as xanthan hydride (Tetrahedron Letters, 32, 3005 (1991); J. Am. Chem. Soc. 112, 1253 (1990); PCT/WO98/54198).

As controlled pore glass (CPG) to be used in a DNA synthesizer, 2'-O-methylnucleoside-bound CPG is commercially available. As regards 2'-O,4'-C-methyleneguanosine, 2'-O,4'-C-methyleneadenosine, 5-methylcytosine and 5-methylthymidine, they may be prepared according to the method described in WO99/14226; and as regards 2'-O,4'-C-alkyleneguanosine, 2'-O,4'-C-alkyleneadenosine, 5-methylcytosine and 5-methylthymidine in which the carbon number of the alkylene group is 2-5, they may be prepared according to the method described in WO00/47599. The thus prepared nucleosides may be bound to CPG as previously described (Oligonucleotide Synthesis, Edited by M. J. Gait, Oxford University Press, 1984). By using the modified CPG (as disclosed in Example 12b of Japanese Unexamined Patent Publication No. Hei7-87982), an oligonucleotide in which a 2-hydroxyethylphosphate group is bound at the 3' end can be synthesized. If 3'-amino-Modifier C3 CPG, 3'-amino-Modifier C7 CPG or Glyceryl CPG (Glen Research) or 3'-specer C3 SynBase CPG 1000 or 3'-specer C9 SynBase CPG 1000 (Link Technologies) is used, an oligonucleotide in which a hydroxyalkylphosphate group or aminoalkylphosphate group is bound at the 3' end can be synthesized.

When the antisense oligonucleotide of the present invention, a pharmaceutically acceptable salt thereof, a solvate thereof or a prodrug thereof is used for cancer treatment, they may be administered per se or mixed with appropriate, pharmaceutically acceptable excipients, diluents, and the like for oral administration in the form of tablets, capsules, granules, powders, syrups, etc. or for parenteral administration in the form of injections, suppositories, patches or external preparations.

These formulations may be prepared by well-known methods using additives such as excipients (e.g., organic excipients including sugar derivatives such as lactose, sucrose, glucose, mannitol or sorbitol; starch derivatives such as corn starch, potato starch, α-starch or dextrin; cellulose derivatives such as crystalline cellulose; gum arabic; dextran; or pullulan; and inorganic excipients including silicate derivatives such as light anhydrous silicic acid, synthetic aluminum silicate, calcium silicate or magnesium aluminometasilicate; phosphates such as calcium hydrogenphosphate; carbonates such as calcium carbonate; and sulfates such as calcium sulfate), lubricants (e.g., stearic acid; metal salts of stearic acid such as calcium stearate and magnesium stearate; talc; colloidal silica; waxes such as beeswax and spermaceti; boric acid; adipic acid; sulfates such as sodium sulfate; glycol; fumaric acid; sodium benzoate; DL-leucine; lauryl sulfates such as sodium lauryl sulfate or magnesium lauryl sulfate; silicic acid compounds such as silicic anhydride and silicic hydrate; or the starch derivatives listed above), binders (e.g., hydroxypropylcellulose, hydroxypropylmethylcellulose, polyvinylpyrrolidone, macrogol, or compounds similar to the above-listed excipients), disintegrants (e.g., cellulose derivatives such as low-substituted hydroxypropylcellulose, carboxymethylcellulose, calcium carboxymethylcellulose or internally crosslinked sodium carboxymethylcellulose; and chemically modified starch/cellulose derivatives such as carboxymethylstarch, sodium carboxymethylstarch or crosslinked polyvinylpyrrolidone), emulsifiers (e.g., colloidal clay such as bentonite or veegum; metal hydroxides such as magnesium hydroxide or aluminum hydroxide; anionic surfactants such as sodium lauryl sulfate or calcium stearate; cationic surfactants such as benzalkonium chloride; or nonionic surfactants such as polyoxyethylenealkylether, polyoxyethylene sorbitan fatty acid ester or sucrose esters of fatty acids), stabilizers (e.g., p-hydroxybenzoate esters such as methylparaben or propylparaben; alcohols such as chlorobutanol, benzyl alcohol or phenylethyl alcohol; benzalkonium chloride; phenols such as phenol or cresol; thimerosal; dehydroacetic acid; or sorbic acid), flavoring agents (e.g., conventionally used sweeteners, acidifiers, flavors and the like) or diluents.

The drug for cancer treatment of the present invention comprises preferably 0.05-5 μmoles/ml, more preferably 0.1-1 μmole/ml of antisense oligonucleotide, pharmaceutically acceptable salt thereof, solvate thereof or prodrug thereof; 0.02-10% w/v of carbohydrate or polyalcohol; and 0.01-0.4% w/v of pharmacologically acceptable surfactant.

As the above carbohydrate, monosaccharides and/or disaccharides are especially preferable. Specific examples of these carbohydrates and polyalcohols include, but are not limited to, glucose, galactose, mannose, lactose, maltose, mannitol and sorbitol. These may be used alone or in combination.

Preferable examples of the surfactant include, but are not limited to, polyoxyethylene sorbitan mono-, di- or tri-ester, alkylphenylpolyoxyethylene, sodium taurocholate, sodium cholate and polyalcohol esters. Among these, polyoxyethylene sorbitan mono-, di- and tri-ester are especially preferable; the most preferable esters are oleate, laurate, stearate and palmitate. These may be used alone or in combination.

More preferably, the drug for cancer treatment of the present invention comprises 0.03-0.09 M pharmacologically acceptable neutral salt such as sodium chloride, potassium chloride and/or calcium chloride.

Even more preferably, the drug for cancer treatment of the present invention may comprise 0.002-0.05 M pharmacologically acceptable buffer. Examples of a preferable buffer include, but are not limited to, sodium citrate, sodium glycinate, sodium phosphate and tris(hydroxymethyl)aminomethane. These buffers may be used alone or in combination.

Further, the above-described drug may be supplied in a state of solution. However, as in the case where there is a need for storage over a certain period of time, the drug is preferably lyophilized for stabilizing the antisense oligonucleotide to thereby prevent the lowering of its therapeutic effect. When lyophilized, the drug may be reconstructed with a solution, such as distilled water for injection, just before use. Thus, the drug is returned into the state of a liquid to be administered. Therefore, the drug for cancer treatment of the present invention encompasses one in a lyophilized state that is used after reconstruction with a solution so that the respective components fall within specified concentration ranges. For the purpose of promoting the solubility of the lyophilized product, the drug may further comprise albumin and amino acids such as glycine.

When the antisense oligonucleotide of the invention, a pharmaceutically acceptable salt thereof, a solvate thereof or a prodrug thereof is administered to a human, the antisense oligonucleotide or the like may be administered, for example, at approximately 0.1-100 mg/kg (body weight), preferably at 1-50 mg/kg (body weight) per adult per day orally or intravenously. This dose may be administered once or may be divided into several times a day. The dose and the number of times of administration may be changed appropriately depending on the type and symptoms of the disease, the age of the patient, administration route, etc.

Administration of the antisense oligonucleotide of the invention, a pharmaceutically acceptable salt thereof, a solvate thereof or a prodrug thereof to cancer patients may be performed, for example, as described below. Briefly, the antisense oligonucleotide, pharmaceutically acceptable salt thereof, solvate thereof or prodrug thereof is prepared by methods well-known to one of ordinary skill in the art and sterilized by conventional methods to prepare, for example, 1200 μg/ml of an injection solution. This solution is instilled to a patient intravenously in the form of, for example, infusion so that the dose of the antisense oligonucleotide is, for example, 20 mg per kg body weight. This administration is repeated, for example, 4 times at intervals of 2 weeks. Subsequently, this treatment is appropriately repeated while confirming the tumor reduction effect as by tumor measurement through physical examination, X-ray photographs, CT and MRI images, ultrasonic examination, confirmation with endoscope and laparoscope, evaluation with tumor markers, cytology and histology.

The present invention also provides an oligonucleotide of 20-23 bp having the entirety or a part of any one of the nucleotide sequences as shown in SEQ ID NOS: 1 to 19, a pharmaceutically acceptable salt thereof, a solvate thereof or a prodrug thereof.

The oligonucleotide of the present invention may advantageously comprise at least one modified nucleotide. The modified oligonucleotide is as described above. D-Ribofuranose constituting the modified nucleotide may advantageously be 2'-O,4-C-alkylenated (e.g., 2'-O,4-C-ethylenated, 2'-O,4-C-methylenated, 2'-O,4-C-propylenated, 2'-O,4-C-tetramethylenated or 2'-O,4-C-pentamethylenated).

The oligonucleotide of the present invention may be an antisense oligonucleotide targeting variant exon(s) of CD44 gene.

The oligonucleotide of the present invention may be prepared according to the method described above for the preparation of antisense oligonucleotide. The pharmaceutically acceptable salts, solvates and prodrugs of the oligonucleotide of the present invention are the same as described for such salts, solvates and prodrugs of the antisense oligonucleotide.

The oligonucleotide of the present invention is capable of inducing skipping of at least one variant exon selected from the group consisting of variant exons 8, 9 and 10 of CD44 gene. Therefore, the present invention also provides a drug for inducing skipping of at least one variant exon selected from the group consisting of variant exons 8, 9 and 10 of CD44 gene, comprising the above-described oligonucleotide, a pharmaceutically acceptable salt thereof, a solvate thereof or a prodrug thereof. The skipping induction drug of the present invention may be used as a medicine or a reagent for experiments.

EXAMPLES

Hereinbelow, the present invention will be described in detail with reference to the following Examples. However, the present invention is not limited to these Examples.

[Example 1] Synthesis of Antisense Oligonucleotides (AOs)

The antisense oligonucleotides (AOs) as shown in Table 1 were synthesized. The locations of AO sequences complementary to CD44 variant mRNA are shown in FIGS. 3 to 5. Modified nucleic acid ENA™ (2'-O,4'-C-Ethylene-bridged Nucleic Acids) was introduced into C (cytosine) and T (thymine) in AO sequences to provide improved affinity and stability.

TABLE 1

| Abbreviation | Designation | AO sequence |
|---|---|---|
| AO-#1 | AOE44E13-0120 | 5'-actatgactggagtccatat-3' (SEQ ID NO: 1) |
| AO-#2 | AOE44E13-2320 | 5'-ttgcagtaggctgaagcgtt-3' (SEQ ID NO: 2) |
| AO-#3 | AOE44E13-4020 | 5'-caaacctgtgtttggatttg-3' (SEQ ID NO: 3) |
| AO-#4 | AOE44E13-7020 | 5'-aagaggtcctgtcctgtcca-3' (SEQ ID NO: 4) |
| AO-#5 | AOE44E14-0120 | 5'-gctctgagaattactctgct-3' (SEQ ID NO: 5) |
| AO-#6 | AOE44E14-2020 | 5'-cttcatgtgatgtagagaag-3' (SEQ ID NO: 6) |
| AO-#7 | AOE44E14-3020 | 5'-tatccaagccttcatgtga-3' (SEQ ID NO: 7) |
| AO-#8 | AOE44E14-4420 | 5'-gatggtattatatatcc-3' (SEQ ID NO: 8) |
| AO-#9 | AOE44E14-5720 | 5'-gtagaagttgttggatggtc-3' (SEQ ID NO: 9) |
| AO-#10 | AOE44E14-7120 | 5'-tgcttgatgtcagagtagaa-3' (SEQ ID NO: 10) |
| AO-#11 | AOE44E15-9420 | 5'-gaaggtcctgattccttcg-3' (SEQ ID NO: 11) |
| AO-#12 | AOE44E13-4420 | 5'-ccaccaaacctgtgtttgga-3' (SEQ ID NO: 12) |
| AO-#13 | AOE44E13-5720 | 5'-ctgtccaaatatccaccaa-3' (SEQ ID NO: 13) |
| AO-#14 | AOE44E13-8320 | 5'-gcgttgtcattgaaagaggt-3' (SEQ ID NO: 14) |
| AO-#15 | AOE44E14-2820 | 5'-ttccaagccttcatgtgatg-3' (SEQ ID NO: 15) |
| AO-#16 | AOE44E15-1320 | 5'-gtctatcttccacctgtga-3' (SEQ ID NO: 16) |

TABLE 1-continued

| Abbreviation | Designation | AO sequence |
|---|---|---|
| AO-#17 | AOE44E15-4920 | 5'-ttccagtaaagtagttgagc-3' (SEQ ID NO: 17) |
| AO-#18 | AOE44E15-13020 | 5'-tccaaaggacccagtatag-3' (SEQ ID NO: 18) |
| AO-#19 | AOE44E15-16020 | 5'-gttggaatctccaacagtaa-3' (SEQ ID NO: 19) |

Synthesis of HO-ACTATGACTGGAGTCCATAT-OH (AO-#1)

Synthesis was performed with an automated nucleic acid synthesizer (DNA/RNA synthesizer model NTS H-8: Nihon Techno Service Co., Ltd.) at 1 µmol scale. Concentrations of solvents, reagents and phosphoramidites in each synthesis cycle were the same as those concentrations used in natural oligonucleotide synthesis. Reagents and 2'-O-methylnucleoside phosphoramidites (for adenosine: Product No. 10-3100-10; for guanosine: Product No. 10-3121-10; for cytidine: Product No. 10-3110-10; and for uridine: Product No. 10-3130-10) were available from Glen Research. Solvents used were products from Wako Pure Chemical Industries. Non-natural phosphoramidites used were the following compounds disclosed in Japanese Unexamined Patent Publication No. 2000-297097 at Example 22 (5'-O-dimethoxytrityl-2'-O,4'-C-ethylene-4-N-benzoyl-5-methylcytidine-3'-O-(2-cyanoethyl N,N-diisopropyl)phosphoramidite) and Example 9 (5'-O-dimethoxytrityl-2'-O,4'-C-ethylene-5-methyluridine-3'-O-(2-cyanoethyl N,N-diisopropyl)phosphoramidite). As a solid carrier, controlled pore glass (CPG) (Product No. BG5-3400-B; Biosearch) was used. Thus, the titled compound was synthesized. It should be noted here that 15 minutes was set as the time required for condensation of amidites.

Protected oligonucleotide analogs with a sequence of interest were treated with thick aqueous ammonia to thereby cut out oligomers from the support and, at the same time, remove the protective group cyanoethyl on phosphorus atoms and the protective group on nucleobases. The solvent was evaporated under reduced pressure; the remaining residue was purified by reversed phase HPLC [(LC-8A from Shimadzu Corporation; column (Shiseido CAPCELLPAK ODS type MG (20×250 mm)); Solution A: 0.1M triethylamine acetate aqueous solution (TEAA), pH 7.0; Solution B: acetonitrile, B %: from 5% to 40% (30 min, linear gradient); 40° C.; 19 mL/min; 260 nm]. Acetic acid was added to the thus purified product to give a final concentration of 10%. The reaction solution was left standing for overnight to remove DMTr groups. After distilling off the solvent, the remaining residue was dissolved in 1.0 mL of water, purified with NAP-10 columns (Product No. 17-0854-01 manufactured by GE Health Care) and lyophilized to thereby obtain a compound of interest.

The subject compound was identified by negative-ion MALDI-TOFMS (calculated value: 6891.8; measured value: 6895.51).

The nucleotide sequence of the subject compound is a sequence complementary to nucleotide Nos. 35228064 to 35228083 of CD44 cDNA (Gene Bank Accession No. NC_018922.2).

Synthesis of HO-TTGCAGTAGGCTGAAGCGTT-OH (AO-#2)

Compound of Example 2 with a sequence of interest was synthesized in the same manner as described for Compound of Example 1. After deprotection, the resultant product was purified by reversed phase HPLC [(LC-8A from Shimadzu Corporation; column (Shiseido CAPCELLPAK ODS type MG (20×250 mm)); Solution A: 0.1M triethylamine acetate aqueous solution (TEAA), pH 7.0; Solution B: acetonitrile, B %: from 5% to 40% (30 min, linear gradient); 40° C.; 19 mL/min; 260 nm]. Acetic acid was added to the thus purified product to give a final concentration of 10%. The reaction solution was left standing for overnight to remove DMTr groups. After distilling off the solvent, the remaining residue was dissolved in 1.0 mL of water, purified with NAP-10 columns (Product No. 17-0854-01 manufactured by GE Health Care) and lyophilized to thereby obtain a compound of interest.

The subject compound was identified by negative-ion MALDI-TOFMS (calculated value: 6937.8; measured value: 6936.09).

The nucleotide sequence of the subject compound is a sequence complementary to nucleotide Nos. 35228086 to 35228105 of CD44 cDNA (Gene Bank Accession No. NC_018922.2).

Synthesis of HO-CAAACCTGTGTTTGGATTTG-OH (AO-#3)

Compound of Example 3 with a sequence of interest was synthesized in the same manner as described for Compound of Example 1. After deprotection, the resultant product was purified by reversed phase HPLC [(LC-8A from Shimadzu Corporation; column (Shiseido CAPCELLPAK ODS type MG (20×250 mm)); Solution A: 0.1M triethylamine acetate aqueous solution (TEAA), pH 7.0; Solution B: acetonitrile, B %: from 5% to 40% (30 min, linear gradient); 40° C.; 19 mL/min; 260 nm]. Acetic acid was added to the thus purified product to give a final concentration of 10%. The reaction solution was left standing for overnight to remove DMTr groups. After distilling off the solvent, the remaining residue was dissolved in 1.0 mL of water, purified with NAP-10 columns (Product No. 17-0854-01 manufactured by GE Health Care) and lyophilized to thereby obtain a compound of interest.

The subject compound was identified by negative-ion MALDI-TOFMS (calculated value: 6911.7; measured value: 6910.09).

The nucleotide sequence of the subject compound is a sequence complementary to nucleotide Nos. 35228103 to 35228122 of CD44 cDNA (Gene Bank Accession No. NC_018922.2).

Synthesis of HO-AAGAGGTCCTGTCCTGTCCA-OH (AO-#4)

Compound of Example 4 with a sequence of interest was synthesized in the same manner as described for Compound of Example 1. After deprotection, the resultant product was purified by reversed phase HPLC [(LC-8A from Shimadzu Corporation; column (Shiseido CAPCELLPAK ODS type MG (20×250 mm)); Solution A: 0.1M triethylamine acetate aqueous solution (TEAA), pH 7.0; Solution B: acetonitrile, B %: from 5% to 40% (30 min, linear gradient); 40° C.; 19 mL/min; 260 nm]. Acetic acid was added to the thus purified product to give a final concentration of 10%. The reaction solution was left standing for overnight to remove DMTr groups. After distilling off the solvent, the remaining residue was dissolved in 1.0 mL of water, purified with NAP-10 columns (Product No. 17-0854-01 manufactured by GE Health Care) and lyophilized to thereby obtain a compound of interest.

The subject compound was identified by negative-ion MALDI-TOFMS (calculated value: 6908.9; measured value: 6907.10).

The nucleotide sequence of the subject compound is a sequence complementary to nucleotide Nos. 35228133 to 35228152 of CD44 cDNA (Gene Bank Accession No. NC_018922.2).

Synthesis of HO-GCTCTGAGAATTACTCTGCT-OH (AO-#5)

Compound of Example 5 with a sequence of interest was synthesized in the same manner as described for Compound of Example 1. After deprotection, the resultant product was purified by reversed phase HPLC [(LC-8A from Shimadzu Corporation; column (Shiseido CAPCELLPAK ODS type MG (20×250 mm)); Solution A: 0.1M triethylamine acetate aqueous solution (TEAA), pH 7.0; Solution B: acetonitrile, B %: from 5% to 40% (30 min, linear gradient); 40° C.; 19 mL/min; 260 nm]. Acetic acid was added to the thus purified product to give a final concentration of 10%. The reaction solution was left standing for overnight to remove DMTr groups. After distilling off the solvent, the remaining residue was dissolved in 1.0 mL of water, purified with NAP-10 columns (Product No. 17-0854-01 manufactured by GE Health Care) and lyophilized to thereby obtain a compound of interest.

The subject compound was identified by negative-ion MALDI-TOFMS (calculated value: 6896.8; measured value: 6899.98).

The nucleotide sequence of the subject compound is a sequence complementary to nucleotide Nos. 35229924 to 35229943 of CD44 cDNA (Gene Bank Accession No. NC_018922.2).

Synthesis of HO-CTTCATGTGATGTAGAGAAG-OH (AO-#6)

Compound of Example 6 with a sequence of interest was synthesized in the same manner as described for Compound of Example 1. After deprotection, the resultant product was purified by reversed phase HPLC [(LC-8A from Shimadzu Corporation; column (Shiseido CAPCELLPAK ODS type MG (20×250 mm)); Solution A: 0.1M triethylamine acetate aqueous solution (TEAA), pH 7.0; Solution B: acetonitrile, B %: from 5% to 40% (30 min, linear gradient); 40° C.; 19 mL/min; 260 nm]. Acetic acid was added to the thus purified product to give a final concentration of 10%. The reaction solution was left standing for overnight to remove DMTr groups. After distilling off the solvent, the remaining residue was dissolved in 1.0 mL of water, purified with NAP-10 columns (Product No. 17-0854-01 manufactured by GE Health Care) and lyophilized to thereby obtain a compound of interest.

The subject compound was identified by negative-ion MALDI-TOFMS (calculated value: 6919.7; measured value: 6920.35).

The nucleotide sequence of the subject compound is a sequence complementary to nucleotide Nos. 35229943 to 35229962 of CD44 cDNA (Gene Bank Accession No. NC_018922.2).

Synthesis of HO-TCTTCCAAGCCTTCATGTGA-OH (AO-#7)

Compound of Example 7 with a sequence of interest was synthesized in the same manner as described for Compound of Example 1. After deprotection, the resultant product was purified by reversed phase HPLC [(LC-8A from Shimadzu Corporation; column (Shiseido CAPCELLPAK ODS type MG (20×250 mm)); Solution A: 0.1M triethylamine acetate aqueous solution (TEAA), pH 7.0; Solution B: acetonitrile, B %: from 5% to 40% (30 min, linear gradient); 40° C.; 19 mL/min; 260 nm]. Acetic acid was added to the thus purified product to give a final concentration of 10%. The reaction solution was left standing for overnight to remove DMTr groups. After distilling off the solvent, the remaining residue was dissolved in 1.0 mL of water, purified with NAP-10 columns (Product No. 17-0854-01 manufactured by GE Health Care) and lyophilized to thereby obtain a compound of interest.

The subject compound was identified by negative-ion MALDI-TOFMS (calculated value: 6882.9; measured value: 6883.40).

The nucleotide sequence of the subject compound is a sequence complementary to nucleotide Nos. 35229953 to 35229972 of CD44 cDNA (Gene Bank Accession No. NC_018922.2).

Synthesis of HO-GATGGTCTTTATCTTCTTCC-OH (AO-#8)

Compound of Example 8 with a sequence of interest was synthesized in the same manner as described for Compound of Example 1. After deprotection, the resultant product was purified by reversed phase HPLC [(LC-8A from Shimadzu Corporation; column (Shiseido CAPCELLPAK ODS type MG (20×250 mm)); Solution A: 0.1M triethylamine acetate aqueous solution (TEAA), pH 7.0; Solution B: acetonitrile, B %: from 5% to 40% (30 min, linear gradient); 40° C.; 19 mL/min; 260 nm]. Acetic acid was added to the thus purified product to give a final concentration of 10%. The reaction solution was left standing for overnight to remove DMTr groups. After distilling off the solvent, the remaining residue was dissolved in 1.0 mL of water, purified with NAP-10 columns (Product No. 17-0854-01 manufactured by GE Health Care) and lyophilized to thereby obtain a compound of interest. The subject compound was identified by negative-ion MALDI-TOFMS (calculated value: 6889.7; measured value: 6888.40).

The nucleotide sequence of the subject compound is a sequence complementary to nucleotide Nos. 35229967 to 35229986 of CD44 cDNA (Gene Bank Accession No. NC_018922.2).

Synthesis of HO-GTAGAAGTTGTTGGATGGTC-OH (AO-#9)

Compound of Example 9 with a sequence of interest was synthesized in the same manner as described for Compound of Example 1. After deprotection, the resultant product was purified by reversed phase HPLC [(LC-8A from Shimadzu Corporation; column (Shiseido CAPCELLPAK ODS type MG (20×250 mm)); Solution A: 0.1M triethylamine acetate aqueous solution (TEAA), pH 7.0; Solution B: acetonitrile, B %: from 5% to 40% (30 min, linear gradient); 40° C.; 19 mL/min; 260 nm]. Acetic acid was added to the thus purified product to give a final concentration of 10%. The reaction solution was left standing for overnight to remove DMTr groups. After distilling off the solvent, the remaining residue was dissolved in 1.0 mL of water, purified with NAP-10 columns (Product No. 17-0854-01 manufactured by GE Health Care) and lyophilized to thereby obtain a compound of interest.

The subject compound was identified by negative-ion MALDI-TOFMS (calculated value: 6952.7; measured value: 6953.62).

The nucleotide sequence of the subject compound is a sequence complementary to nucleotide Nos. 35229980 to 35229999 of CD44 cDNA (Gene Bank Accession No. NC_018922.2).

Synthesis of HO-TGCTTGATGTCAGAGTAGAA-OH (AO-#10)

Compound of Example 10 with a sequence of interest was synthesized in the same manner as described for Compound of Example 1. After deprotection, the resultant product was purified by reversed phase HPLC [(LC-8A from Shimadzu Corporation; column (Shiseido CAPCELLPAK ODS type MG (20×250 mm)); Solution A: 0.1M triethylamine acetate aqueous solution (TEAA), pH 7.0; Solution B: acetonitrile, B %: from 5% to 40% (30 min, linear gradient); 40° C.; 19 mL/min; 260 nm]. Acetic acid was added to the thus purified product to give a final concentration of 10%. The reaction solution was left standing for overnight to remove DMTr groups. After distilling off the solvent, the remaining residue was dissolved in 1.0 mL of water, purified with NAP-10 columns (Product No. 17-0854-01 manufactured by GE Health Care) and lyophilized to thereby obtain a compound of interest.

The subject compound was identified by negative-ion MALDI-TOFMS (calculated value: 6919.7; measured value: 6922.82).

The nucleotide sequence of the subject compound is a sequence complementary to nucleotide Nos. 35229994 to 35230013 of CD44 cDNA (Gene Bank Accession No. NC_018922.2).

Synthesis of HO-GAAGGTCCTGCTTTCCTTCG-OH (AO-#11)

Compound of Example 11 with a sequence of interest was synthesized in the same manner as described for Compound of Example 1. After deprotection, the resultant product was purified by reversed phase HPLC [(LC-8A from Shimadzu Corporation; column (Shiseido CAPCELLPAK ODS type MG (20×250 mm)); Solution A: 0.1M triethylamine acetate aqueous solution (TEAA), pH 7.0; Solution B: acetonitrile, B %: from 5% to 40% (30 min, linear gradient); 40° C.; 19 mL/min; 260 nm]. Acetic acid was added to the thus purified product to give a final concentration of 10%. The reaction solution was left standing for overnight to remove DMTr groups. After distilling off the solvent, the remaining residue was dissolved in 1.0 mL of water, purified with NAP-10 columns (Product No. 17-0854-01 manufactured by GE Health Care) and lyophilized to thereby obtain a compound of interest.

The subject compound was identified by negative-ion MALDI-TOFMS (calculated value: 6914.9; measured value: 6916.37).

The nucleotide sequence of the subject compound is a sequence complementary to nucleotide Nos. 35231298 to 35231317 of CD44 cDNA (Gene Bank Accession No. NC 018922.2).

Synthesis of HO-CCACCAAACCTGTGTTTGGA-OH (AO-#12)

Compound of Example 12 with a sequence of interest was synthesized in the same manner as described for Compound of Example 1. After deprotection, the resultant product was purified by reversed phase HPLC [(LC-8A from Shimadzu Corporation; column (Shiseido CAPCELLPAK ODS type MG (20×250 mm)); Solution A: 0.1M triethylamine acetate aqueous solution (TEAA), pH 7.0; Solution B: acetonitrile, B %: from 5% to 40% (30 min, linear gradient); 40° C.; 19 mL/min; 260 nm]. Acetic acid was added to the thus purified product to give a final concentration of 10%. The reaction solution was left standing for overnight to remove DMTr groups. After distilling off the solvent, the remaining residue was dissolved in 1.0 mL of water, purified with NAP-10 columns (Product No. 17-0854-01 manufactured by GE Health Care) and lyophilized to thereby obtain a compound of interest.

The subject compound was identified by negative-ion MALDI-TOFMS (calculated value: 6892.9; measured value: 6893.44).

The nucleotide sequence of the subject compound is a sequence complementary to nucleotide Nos. 35208148 to 35208167 of CD44 cDNA (Gene Bank Accession No. NC_000011.10).

Synthesis of HO-CTGTCCAAATCTTCCACCAA-OH (AO-#13)

Compound of Example 13 with a sequence of interest was synthesized in the same manner as described for Compound of Example 1. After deprotection, the resultant product was purified by reversed phase HPLC [(LC-8A from Shimadzu Corporation; column (Shiseido CAPCELLPAK ODS type MG (20×250 mm)); Solution A: 0.1M triethylamine acetate aqueous solution (TEAA), pH 7.0; Solution B: acetonitrile, B %: from 5% to 40% (30 min, linear gradient); 40° C.; 19 mL/min; 260 nm]. Acetic acid was added to the thus purified product to give a final concentration of 10%. The reaction solution was left standing for overnight to remove DMTr groups. After evaporation of the solvent, the remaining residue was dissolved in 1.0 mL of water, purified with NAP-10 columns (Product No. 17-0854-01 manufactured by GE Health Care) and lyophilized to thereby obtain a compound of interest.

The subject compound was identified by negative-ion MALDI-TOFMS (calculated value: 6848.99; measured value: 6850.18).

The nucleotide sequence of the subject compound is a sequence complementary to nucleotide Nos. 35208161 to 35208180 of CD44 cDNA (Gene Bank Accession No. NC_000011.10).

Synthesis of HO-GCGTTGTCATTGAAAGAGGT-OH (AO-#14)

Compound of Example 14 with a sequence of interest was synthesized in the same manner as described for Compound of Example 1. After deprotection, the resultant product was purified by reversed phase HPLC [(LC-8A from Shimadzu Corporation; column (Shiseido CAPCELLPAK ODS type MG (20×250 mm)); Solution A: 0.1M triethylamine acetate aqueous solution (TEAA), pH 7.0; Solution B: acetonitrile, B %: from 5% to 40% (30 min, linear gradient); 40° C.; 19 mL/min; 260 nm]. Acetic acid was added to the thus purified product to give a final concentration of 10%. The reaction solution was left standing for overnight to remove DMTr groups. After distilling off the solvent, the remaining residue was dissolved in 1.0 mL of water, purified with NAP-10 columns (Product No. 17-0854-01 manufactured by GE Health Care) and lyophilized to thereby obtain a compound of interest.

The subject compound was identified by negative-ion MALDI-TOFMS (calculated value: 6935.72; measured value: 6936.96).

The nucleotide sequence of the subject compound is a sequence complementary to nucleotide Nos. 35208187 to 35208206 of CD44 cDNA (Gene Bank Accession No. NC_000011.10).

Synthesis of HO-TTCCAAGCCTTCATGTGATG-OH (AO-#15)

Compound of Example 15 with a sequence of interest was synthesized in the same manner as described for Compound of Example 1. After deprotection, the resultant product was purified by reversed phase HPLC [(LC-8A from Shimadzu Corporation; column (Shiseido CAPCELLPAK ODS type MG (20×250 mm)); Solution A: 0.1M triethylamine acetate aqueous solution (TEAA), pH 7.0; Solution B: acetonitrile, B %: from 5% to 40% (30 min, linear gradient); 40° C.; 19 mL/min; 260 nm]. Acetic acid was added to the thus purified product to give a final concentration of 10%. The reaction solution was left standing for overnight to remove DMTr groups. After distilling off the solvent, the remaining residue was dissolved in 1.0 mL of water, purified with NAP-10 columns (Product No. 17-0854-01 manufactured by GE Health Care) and lyophilized to thereby obtain a compound of interest.

The subject compound was identified by negative-ion MALDI-TOFMS (calculated value: 6896.8; measured value: 6896.38).

The nucleotide sequence of the subject compound is a sequence complementary to nucleotide Nos. 35209992 to 35210011 of CD44 cDNA (Gene Bank Accession No. NC_000011.10).

Synthesis of HO-GTCTCTTCTTCCACCTGTGA-OH (AO-#16)

Compound of Example 16 with a sequence of interest was synthesized in the same manner as described for Compound of Example 1. After deprotection, the resultant product was purified by reversed phase HPLC [(LC-8A from Shimadzu Corporation; column (Shiseido CAPCELLPAK ODS type MG (20×250 mm)); Solution A: 0.1M triethylamine acetate aqueous solution (TEAA), pH 7.0; Solution B: acetonitrile, B %: from 5% to 40% (30 min, linear gradient); 40° C.; 19 mL/min; 260 nm]. Acetic acid was added to the thus purified product to give a final concentration of 10%. The reaction solution was left standing for overnight to remove DMTr groups. After distilling off the solvent, the remaining residue was dissolved in 1.0 mL of water, purified with NAP-10 columns (Product No. 17-0854-01 manufactured by GE Health Care) and lyophilized to thereby obtain a compound of interest.

The subject compound was identified by negative-ion MALDI-TOFMS (calculated value: 6887.86; measured value: 6889.15).

The nucleotide sequence of the subject compound is a sequence complementary to nucleotide Nos. 35211258 to 35211277 of CD44 cDNA (Gene Bank Accession No. NC_000011.10).

Synthesis of HO-TTCCAGTAAAGTAGTTGAGC-OH (AO-#17)

Compound of Example 17 with a sequence of interest was synthesized in the same manner as described for Compound of Example 1. After deprotection, the resultant product was purified by reversed phase HPLC [(LC-8A from Shimadzu Corporation; column (Shiseido CAPCELLPAK ODS type MG (20×250 mm)); Solution A: 0.1M triethylamine acetate aqueous solution (TEAA), pH 7.0; Solution B: acetonitrile, B %: from 5% to 40% (30 min, linear gradient); 40° C.; 19 mL/min; 260 nm]. Acetic acid was added to the thus purified product to give a final concentration of 10%. The reaction solution was left standing for overnight to remove DMTr groups. After distilling off the solvent, the remaining residue was dissolved in 1.0 mL of water, purified with NAP-10 columns (Product No. 17-0854-01 manufactured by GE Health Care) and lyophilized to thereby obtain a compound of interest.

The subject compound was identified by negative-ion MALDI-TOFMS (calculated value: 6905.76; measured value: 6907.01).

The nucleotide sequence of the subject compound is a sequence complementary to nucleotide Nos. 35211294 to 35211313 of CD44 cDNA (Gene Bank Accession No. NC_000011.10).

Synthesis of HO-TCCAAAGGACCCAGTCTTAG-OH (AO-#18)

Compound of Example 18 with a sequence of interest was synthesized in the same manner as described for Compound of Example 1. After deprotection, the resultant product was purified by reversed phase HPLC [(LC-8A from Shimadzu Corporation; column (Shiseido CAPCELLPAK ODS type MG (20×250 mm)); Solution A: 0.1M triethylamine acetate aqueous solution (TEAA), pH 7.0; Solution B: acetonitrile, B %: from 5% to 40% (30 min, linear gradient); 40° C.; 19 mL/min; 260 nm]. Acetic acid was added to the thus purified product to give a final concentration of 10%. The reaction solution was left standing for overnight to remove DMTr groups. After distilling off the solvent, the remaining residue was dissolved in 1.0 mL of water, purified with NAP-10 columns (Product No. 17-0854-01 manufactured by GE Health Care) and lyophilized to thereby obtain a compound of interest.

The subject compound was identified by negative-ion MALDI-TOFMS (calculated value: 6889.94; measured value: 6891.13).

The nucleotide sequence of the subject compound is a sequence complementary to nucleotide Nos. 35211375 to 35211394 of CD44 cDNA (Gene Bank Accession No. NC_000011.10).

Synthesis of HO-GTTGGAATCTCCAACAGTAA-OH (AO-#19)

Compound of Example 19 with a sequence of interest was synthesized in the same manner as described for Compound of Example 1. After deprotection, the resultant product was purified by reversed phase HPLC [(LC-8A from Shimadzu Corporation; column (Shiseido CAPCELLPAK ODS type MG (20×250 mm)); Solution A: 0.1M triethylamine acetate aqueous solution (TEAA), pH 7.0; Solution B: acetonitrile, B %: from 5% to 40% (30 min, linear gradient); 40° C.; 19 mL/min; 260 nm]. Acetic acid was added to the thus purified product to give a final concentration of 10%. The reaction solution was left standing for overnight to remove DMTr groups. After distilling off the solvent, the remaining residue was dissolved in 1.0 mL of water, purified with NAP-10 columns (Product No. 17-0854-01 manufactured by GE Health Care) and lyophilized to thereby obtain a compound of interest.

The subject compound was identified by negative-ion MALDI-TOFMS (calculated value: 6888.83; measured value: 6890.14).

The nucleotide sequence of the subject compound is a sequence complementary to nucleotide Nos. 35211405 to 35211424 of CD44 cDNA (Gene Bank Accession No. NC_000011.10).

[Example 2] Confirmation of the Effect of Exon Skipping Induction by Antisense Oligonucleotides (AOs) in Cancer Stem Cells The following cancer stem cells of colon cancer and gastric cancer were purchased from ATCC (American Type Culture Collection). These cancer stem cells express variant exons of CD44 gene (especially high-yield expression of CD44v8-10).

HT-29 Cells (Colon Cancer)
KATOIII Cells (Gastric Cancer)

These cells were seeded on 12-well plates separately and cultured overnight. AOs (50 or 100 nM) was added to the thus cultured human gastric cancer cells KATOIII. Three hours later, FBS was added and the cells were cultured for 24 additional hours. Subsequently, RNA was recovered, followed by analysis of CD44 mRNA by RT-PCR.

As a result, it was confirmed that addition of AO induced skipping of abnormal exons, resulting in an increased expression of normal CD44s (FIGS. 7, 8 and 9); KATOIII cells usually express CD44v8-10 as a main isoform in which v8, v9 and v10 have been inserted, but as a result of addition of AO, the expression of CD44v8-10 decreased in a concentration dependent manner while the expression of CD44s recovered from about 10% to about 80%. The ratio of expression of CD44s was determined as follows: PCR products were measured with Agilent 2100 bioanalyzer and the measured values were subjected to calculation with the formula CD44s/(CD44s+CD44v)×100. Here, CD44v includes CD44v8-10, CD44v9-10, CD44v8-9 and CD44v8.

FIG. 10 shows the results obtained with AO-#7 (10 nM, 25 nM, 50 nM and 100 nM) that was the most effective (n=3).

FIG. 11 shows the results of FIG. 10 in a graphic form.

The same experiments were performed using HT-29 cells instead of KATOIII cells. As in the results with KATOIII cells, it was confirmed that skipping of abnormal exons was induced, resulting in an increased expression of normal CD44s. The results obtained with AO-#7 are shown in FIG. 12 (HT-29 cells).

Extraction of RNA

RNA was extracted as described below.
1. AO-transfected cells were cultured for 24 hours and washed with PBS once. Then, 300 µL of Lysis/binding buffer (Roche, High Pure RNA Isolation Kit) and 150 µL of PBS were added to the cells.
2. After standing at room temperature for 1 minute, the cell mixture in the wells was collected into tubes.
3. RNA was extracted according to the protocol of High Pure RNA Isolation Kit (Roche).
4. Finally, RNA was eluted with 36 µL of elution buffer.

Reverse Transcription Reaction

Reverse transcription was performed as described below.
1. To 500 ng of RNA, Milli-Q (sterilized) was added to make a 6 µL solution.
2. To the solution of 1 above, 2 µL of random primers (Invitrogen 3 µg/µL diluted 20-fold) and 5 µL of 2.5 mM dNTP mixture (Invitrogen) were added.
3. The resultant solution was heated at 65° C. for 5 minutes.
4. Then, the solution was left standing at 25° C. for 10 minutes.
5. To the above reaction solution, 1 µL of M-MLV-reverse transcriptase (Invitrogen 200 U/µL), 1 µL of RNase OUT (Invitrogen 40 U/µL), 1 µL of 0.1M DTT (attached to M-MLV-reverse transcriptase) and 4 µL of 5xFirst stand Buffer (attached to M-MLV-reverse transcriptase) were added.
6. The reaction solution was kept at 37° C. for 55 minutes and then heated at 70° C. for 15 minutes.
7. The resultant reaction solution was stored at −80° C.

PCR Reaction

PCR reaction was performed as described below.
1. The components listed below were mixed and heated at 94° C. for 3 minutes.
Reverse transcription products 1.0 µL
Forward primer (10 pmol/µL) 0.5 µL
Reverse primer (10 pmol/µL) 0.5 µL
dNTP (attached to TAKARA Ex Taq) 0.8 µL
Buffer (attached to TAKARA Ex Taq) 1.0 µL
Ex Taq 0.05 µL
Sterilized water 6.15 µL
2. After treatment at 94° C. for 3 minutes, 25 cycles of treatments at 94° C. for 30 seconds, 60° C. for 30 seconds and 72° C. for 90 seconds were performed
3. Then, the reaction solution was heated at 72° C. for 3 minutes.

The nucleotide sequences of the forward and reverse primers used in the PCR for detecting a skipping of variant exons are as shown below.

```
Forward primer (CD44 exon 5):
                            (SEQ ID NO: 23)
5'-TCCCAGACGAAGACAGTCCCTGGAT-3'

Reverse primer (CD44 exon 16):
                            (SEQ ID NO: 24)
5'-CACTGGGGTGGAATGTGTCTTGGTC-3'
```

Example 3

KATOIII cells were seeded on 12-well plates at 1×10$^5$ cells/well. AO-#7 (50 nM) or Milli-Q (control) was added using Lipofectamine 2000 reagent (Invitrogen Life Technologies). The plates were left standing for 3 hours in a 37° C., 5% $CO_2$ incubator. Subsequently, 20% FBS-containing IMDM (Iscove's Modified Dulbecco's Medium) (500 µL/well) and CDDP (final concentration 5 µg/mL; Nippon Kayaku Co., Ltd.; Randa Inj. 10 mg/20 mL) were added, followed by further culturing. The plates were equilibrated to room temperature at 24, 48, 72 and 96 hours of culture, and Cell Titer-Glo Reagent (Cell Titer-Glo Luminesent Cell Viability Assay (Promega)) as prepared was added to each well. Then, luciferase emission signals were measured with Multi-label Plate Reader (2030 ARVO X3, PerkinElmer).

The results are shown in FIG. 13. The graph in this Figure was drawn from the values each calculated by taking the value of control as 100%. Addition of CDDP+AO-#7 inhibited cell growth by a greater degree than addition of CDDP (cisplatin) alone.

Example 4

KATOIII cells were seeded on 12-well plates at 1×10$^5$ cells/well. AO-#7 (50 nM) or AO-#12 (50 nM) or Milli-Q (control) was added using Lipofectamine 2000 reagent (Invitrogen Life Technologies). The plates were left standing for 3 hours in a 37° C., 5% $CO_2$ incubator. Subsequently, 20% FBS-containing IMDM (Iscove's Modified Dulbecco's Medium) (500 µL/well) was added, followed by further culturing. The plates were equilibrated to room temperature at 24, 48, 72 and 96 hours of culture, and Cell Titer-Glo Reagent (Cell Titer-Glo™ Luminesent Cell Viability Assay (Promega)) as prepared was added to each well. Then, luciferase emission signals were measured with Multi-label Plate Reader (2030 ARVO X3, PerkinElmer).

The results are shown in FIG. 14. AO-#7 is the AO which was the most effective in inducing the skipping of CD44v mRNA (CD4v8-10), whereas AO-#12 is the AO which scarcely affected the skipping of CD44v mRNA. Milli-Q (water) was used as a control. The toxic effect of AO was confirmed by comparing the results of AO-#7 and AO-#12. Addition of AO-#7 alone inhibited the growth of KATOIII cells.

All publications, patents and patent applications cited herein are incorporated herein by reference in their entirety.

INDUSTRIAL APPLICABILITY

The present invention is applicable to cancer treatment.

SEQUENCE LISTING FREE TEXT

```
<SEQ ID NO: 1>
This shows the nucleotide sequence of AO-#1.      5'-actatgactggagtccatat-3'

<SEQ ID NO: 2>
This shows the nucleotide sequence of AO-#2.      5'-ttgcagtaggctgaagcgtt-3'

<SEQ ID NO: 3>
This shows the nucleotide sequence of AO-#3.      5'-caaacctgtgtttggatttg-3'

<SEQ ID NO: 4>
This shows the nucleotide sequence of AO-#4.      5'-aagaggtcctgtcctgtcca-3'

<SEQ ID NO: 5>
This shows the nucleotide sequence of AO-#5.      5'-gctctgagaattactctgct-3'

<SEQ ID NO: 6>
This shows the nucleotide sequence of AO-#6.      5'-cttcatgtgatgtagagaag-3'

<SEQ ID NO: 7>
This shows the nucleotide sequence of AO-#7.      5'-tcttccaagccttcatgtga-3'

<SEQ ID NO: 8>
This shows the nucleotide sequence of AO-#8.      5'-gatggtctttatcttcttcc-3'

<SEQ ID NO: 9>
This shows the nucleotide sequence of AO-#9       5'-gtagaagttgttggatggtc-3'

<SEQ ID NO: 10>
This shows the nucleotide sequence of AO-#10      5'-tgcttgatgtcagagtagaa-3'

<SEQ ID NO: 11>
This shows the nucleotide sequence of AO-#11      5'-gaaggtcctgcttccttcg-3'

<SEQ ID NO: 12>
This shows the nucleotide sequence of AO-#12      5'-CCACCAAACCTGTGTTTGGA-3'

<SEQ ID NO: 13>
This shows the nucleotide sequence of AO-#13      5'-CTGTCCAAATCTTCCACCAA-3'

<SEQ ID NO: 14>
This shows the nucleotide sequence of AO-#14      5'-GCGTTGTCATTGAAAGAGGT-3'

<SEQ ID NO: 15>
This shows the nucleotide sequence of AO-#15      5'-TTCCAAGCCTTCATGTGATG-3'

<SEQ ID NO: 16>
This shows the nucleotide sequence of AO-#16      5'-GTCTCTTCTTCCACCTGTGA-3'

<SEQ ID NO: 17>
This shows the nucleotide sequence of AO-#17      5'-TTCCAGTAAAGTAGTTGAGC-3'

<SEQ ID NO: 18>
This shows the nucleotide sequence of AO-#18      5'-TCCAAAGGACCCAGTCTTAG-3'

<SEQ ID NO: 19>
This shows the nucleotide sequence of AO-#19      5'-GTTGGAATCTCCAACAGTAA-3'

<SEQ ID NO: 20>
This shows the nucleotide sequence of CD44v8 mRNA.
atatggactccagtcatagtacaacgcttcagcctactgcaaatccaaacacaggtttggtggaagatttggacagg
acaggacctctttcaatgacaacgc <SEQ ID NO: 21>
This shows the nucleotide sequence of CD44v9 mRNA.
agcagagtaattctcagagcttctctacatcacatgaaggcttggaagaagataaagaccatccaacaacttctact
ctgacatcaagca
```

SEQUENCE LISTING FREE TEXT

<SEQ ID NO: 22>
This shows the nucleotide sequence of CD44v10 mRNA.
ataggaatgatgtcacaggtggaagaagagacccaaatcattctgaaggctcaactactttactggaaggttatacc
tctcattacccacacacgaaggaaagcaggaccttcatcccagtgacctcagctaagactgggtcctttggagttac
tgcagttactgttggagattccaactctaatgtcaatcgttccttatcag <SEQ ID NO: 23>
This shows the nucleotide sequence of the forward primer used in PCR reaction
for detecting the skipping of variant exons.
5'-TCCCAGACGAAGACAGTCCCTGGAT-3'

<SEQ ID NO: 24>
This shows the nucleotide sequence of the reverse primer used in PCR reaction
for detecting the skipping of variant exons.
5'-CACTGGGGTGGAATGTGTCTTGGTC-3'

The invention claimed is:

1. A drug for cancer treatment, comprising an antisense oligonucleotide capable of inducing skipping of variant exon(s) of CD44 gene to thereby increase expression of normal CD44 mRNA, a pharmaceutically acceptable salt thereof, a solvate thereof or a prodrug thereof,
wherein the antisense oligonucleotide is an oligonucleotide of 20-23 bp having the entirety of any one of the nucleotide sequences as shown in SEQ ID NOS: 1 to 19, and
wherein the antisense oligonucleotide comprises at least one modified nucleotide.

2. The drug for cancer treatment according to claim 1, which enhances the sensitivity of cancer cells to anticancer agents and/or radiation.

3. The drug for cancer treatment according to claim 1, wherein the at least one modified nucleotide is D-ribofuranose that is 2'-O, 4'-C-alkylenated.

4. An oligonucleotide of 20-23 bp having the entirety of any one of the nucleotide sequences as shown in SEQ ID NOS: 1 to 19, a pharmaceutically acceptable salt thereof, a solvate thereof or a prodrug thereof, and
wherein the oligonucleotide comprises at least one modified nucleotide.

5. The oligonucleotide according to claim 4, wherein the at least one modified nucleotide is D-ribofuranose that is 2'-O, 4'-C-alkylenated.

6. The oligonucleotide according to claim 4 which is an antisense oligonucleotide targeting variant exon(s) of CD44 gene, a pharmaceutically acceptable salt thereof, a solvate thereof or a prodrug thereof.

7. A method of treating cancer expressing at least one variant exon of CD44, comprising:
administering to a subject a pharmaceutically effective amount of the oligonucleotide according to claim 4 capable of inducing skipping of variant exon(s) of CD44 gene to thereby increase expression of normal CD44 mRNA, and
wherein said at least one variant exon of CD44 is CD44v8, CD44v9 and CD44v10.

8. A method of inducing skipping of variant exon(s) of CD44 gene, comprising:
binding the oligonucleotide according to claim 4 to exon(s) of CD44 gene to thereby increase expression of normal CD44 mRNA.

9. The drug for cancer treatment according to claim 1, wherein the antisense oligonucleotide is an oligonucleotide of 20-23 bp having the entirety of the nucleotide sequence as shown in SEQ ID NO: 7.

10. The drug for cancer treatment according to claim 3, wherein the D-ribofuranose that is 2'-O, 4'-C-alkylenated is at least one selected from the group consisting of 2'-O,4'-C-ethylenated, 2'-O,4'-C-methylenated, 2'-O,4'-C-propylenated, 2'-O,4'-C-tetramethylated, and 2'-O,4'-C-pentamethylated.

11. A drug for cancer treatment, comprising an antisense oligonucleotide capable of inducing skipping of variant exon(s) of CD44 gene to thereby increase expression of normal CD44 mRNA, a pharmaceutically acceptable salt thereof, a solvate thereof or a prodrug thereof,
wherein the antisense oligonucleotide is an oligonucleotide having a nucleotide sequence complementary to at least 18 bp and up to the entirety of the nucleotide sequence of variant exon 8, 9 or 10 of CD44 gene, wherein the antisense oligonucleotide having a nucleotide sequence complementary to at least 18 bp and up to the entirety of the nucleotide sequence of variant exon 8, 9 or 10 of CD44 gene is an oligonucleotide of 20-23 bp having the entirety of any one of the nucleotide sequences as shown in SEQ ID NOS: 1 to 19, and
wherein the oligonucleotide comprises at least one modified nucleotide.

12. An oligonucleotide of 20-23 bp having at least 18 and up to the entirety of any one of the nucleotide sequences as shown in SEQ ID NOS: 1 to 19, a pharmaceutically acceptable salt thereof, a solvate thereof or a prodrug thereof, and
wherein the oligonucleotide comprises at least one modified nucleotide.

13. The method of treating cancer according to claim 7, wherein the cancer is at least one selected from the group consisting of gastric cancer, colon cancer, breast cancer, head and neck squamous cell carcinoma.

* * * * *

SEQUENCE LISTING

<160> NUMBER OF SEQ ID NOS: 24

<210> SEQ ID NO 1
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1
actatgactg gagtccatat                                          20

<210> SEQ ID NO 2
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 2
ttgcagtagg ctgaagcgtt                                          20

<210> SEQ ID NO 3
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 3
caaacctgtg tttggatttg                                          20

<210> SEQ ID NO 4
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 4
aagaggtcct gtcctgtcca                                          20

<210> SEQ ID NO 5
<211> LENGTH: 20
<212> TYPE: DNA
<213> ORGANISM: Artificial Sequence

```
<220> FEATURE:
<223> OTHER INFORMATION: synthetic oligonucleotide

<400> SEQUENCE: 5
gctctgagaa ttactctgct                                              20

<210> SEQ ID NO 6
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 6
cttcatgtga tgtagagaag                                              20

<210> SEQ ID NO 7
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 7
tcttccaagc cttcatgtga                                              20

<210> SEQ ID NO 8
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 8
gatggtcttt atcttcttcc                                              20

<210> SEQ ID NO 9
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 9
gtagaagttg ttggatggtc                                              20

<210> SEQ ID NO 10
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 10
tgcttgatgt cagagtagaa                                              20

<210> SEQ ID NO 11
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 11
gaaggtcctg ctttccttcg                                              20
```

<210> SEQ ID NO 12
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 12
ccaccaaacc tgtgtttgga                                                 20

<210> SEQ ID NO 13
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 13
ctgtccaaat cttccaccaa                                                 20

<210> SEQ ID NO 14
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 14
gcgttgtcat tgaaagaggt                                                 20

<210> SEQ ID NO 15
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 15
ttccaagcct tcatgtgatg                                                 20

<210> SEQ ID NO 16
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 16
gtctcttctt ccacctgtga                                                 20

<210> SEQ ID NO 17
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 17
ttccagtaaa gtagttgagc                                                 20

<210> SEQ ID NO 18
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 18
tccaaaggac ccagtcttag                                                20

<210> SEQ ID NO 19
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 19
gttggaatct ccaacagtaa                                                20

<210> SEQ ID NO 20
<211> LENGTH: 102
<212> TYPE: DNA
<213> ORGANISM: Homo sapiens
<220> FEATURE:
<221> NAME/KEY: mRNA
<222> LOCATION: (1)..(102)
<223> OTHER INFORMATION: CD44v8 mRNA

<400> SEQUENCE: 20
atatggactc cagtcatagt acaacgcttc agcctactgc aaatccaaac acaggtttgg   60
tggaagattt ggacaggaca ggacctcttt caatgacaac gc                     102

<210> SEQ ID NO 21
<211> LENGTH: 90
<212> TYPE: DNA
<213> ORGANISM: Homo sapiens
<220> FEATURE:
<221> NAME/KEY: mRNA
<222> LOCATION: (1)..(90)
<223> OTHER INFORMATION: CD44v9 mRNA

<400> SEQUENCE: 21
agcagagtaa ttctcagagc ttctctacat cacatgaagg cttggaagaa gataaagacc   60
atccaacaac ttctactctg acatcaagca                                    90

<210> SEQ ID NO 22
<211> LENGTH: 204
<212> TYPE: DNA
<213> ORGANISM: Homo sapiens
<220> FEATURE:
<221> NAME/KEY: mRNA
<222> LOCATION: (1)..(204)
<223> OTHER INFORMATION: CD44v10 mRNA

<400> SEQUENCE: 22
ataggaatga tgtcacaggt ggaagaagag acccaaatca ttctgaaggc tcaactactt   60
tactggaagg ttatacctct cattacccac acacgaagga aagcaggacc ttcatcccag  120
tgacctcagc taagactggg tcctttggag ttactgcagt tactgttgga gattccaact  180
ctaatgtcaa tcgttcctta tcag                                         204

<210> SEQ ID NO 23
<211> LENGTH: 25
<212> TYPE: DNA
<213> ORGANISM: Artificial Sequence
<220> FEATURE:
<223> OTHER INFORMATION: primer

<400> SEQUENCE: 23

```
tcccagacga agacagtccc tggat                                          25

<210> SEQ ID NO 24
<211> LENGTH: 25
<212> TYPE: DNA
<213> ORGANISM: Artificial Sequence
<220> FEATURE:
<223> OTHER INFORMATION: primer

<400> SEQUENCE: 24
cactggggtg gaatgtgtct tggtc                                          25
```